US009044232B2

(12) United States Patent
Cheng et al.

(10) Patent No.: US 9,044,232 B2
(45) Date of Patent: Jun. 2, 2015

(54) MEDICAL HEATING DEVICE AND METHOD WITH SELF-LIMITING ELECTRICAL HEATING ELEMENT

(75) Inventors: Tai Chun Cheng, Mountain View, CA (US); Elbert T. Cheng, Los Altos, CA (US); Jacqueline T. Cheng, Mountain View, CA (US); Ivy Y. Cheng, Mountain View, CA (US)

(73) Assignee: Curo Medical, Inc., Saratoga, CA (US)

( * ) Notice: Subject to any disclaimer, the term of this patent is extended or adjusted under 35 U.S.C. 154(b) by 872 days.

(21) Appl. No.: 12/652,262

(22) Filed: Jan. 5, 2010

(65) Prior Publication Data
US 2011/0166563 A1    Jul. 7, 2011

(51) Int. Cl.
| A61B 18/08 | (2006.01) |
| A61B 17/32 | (2006.01) |
| A61B 18/14 | (2006.01) |
| A61B 18/00 | (2006.01) |
| A61B 18/18 | (2006.01) |

(52) U.S. Cl.
CPC ....... *A61B 18/082* (2013.01); *A61B 17/320068* (2013.01); *A61B 18/1402* (2013.01); *A61B 18/1477* (2013.01); *A61B 2018/00083* (2013.01); *A61B 2018/00101* (2013.01); *A61B 2018/00136* (2013.01); *A61B 2018/00595* (2013.01); *A61B 2018/00601* (2013.01); *A61B 2018/00702* (2013.01); *A61B 2018/00791* (2013.01); *A61B 2018/00821* (2013.01); *A61B 2018/00875* (2013.01); *A61B 2018/1425* (2013.01); *A61B 2018/1869* (2013.01)

(58) Field of Classification Search
CPC ................. A61B 18/08; A61B 18/082; A61B 2018/00815; A61B 2018/00821; A61B 2018/00005

USPC .................................................. 606/28–31
See application file for complete search history.

(56) References Cited

U.S. PATENT DOCUMENTS

| 4,033,351 | A | | 7/1977 | Hetzel |
| 4,616,660 | A | | 10/1986 | Johns |
| 4,872,458 | A | * | 10/1989 | Kanehira et al. ................ 606/31 |
| 5,383,917 | A | | 1/1995 | Desai et al. |
| 5,462,546 | A | | 10/1995 | Rydell |
| 5,514,131 | A | | 5/1996 | Edwards et al. |

(Continued)

OTHER PUBLICATIONS

U.S. Appl. No. 12/783,714, filed May 20, 2010, Cheng et al.

(Continued)

*Primary Examiner* — Joseph Stoklosa
*Assistant Examiner* — Jocelyn D Ram
(74) *Attorney, Agent, or Firm* — Wilson Sonsini Goodrich & Rosati

(57) ABSTRACT

A medical heating device is based on an electrical heater formed out of a self-limiting conductive material, such as a conductive polymer or ceramic. An electrical resistance that gradually changes with temperature characterizes the material such that heat production from electrical current through the material varies with temperature. A thermally insulating jacket contains the self-limiting heater element, which can be coupled to an electrical power supply. A probe thermally coupled to the heater extends outward from the jacket. The self-limiting medical heating device can be used by touching the end of the probe to target tissue, such as skin, adipose tissue, nerves, glands, vascular tissue, or abnormal growths or tumors to effect the desired treatment, typically by thermally ablating, cutting, or shrinking the target tissue where touched by the probe or in the vicinity therein.

19 Claims, 9 Drawing Sheets

(56) References Cited

U.S. PATENT DOCUMENTS

| | | | |
|---|---|---|---|
| 5,571,153 A * | 11/1996 | Wallsten | 607/98 |
| 5,611,798 A * | 3/1997 | Eggers | 606/31 |
| 5,766,153 A | 6/1998 | Eggers et al. | |
| 5,911,719 A * | 6/1999 | Eggers | 606/31 |
| 5,916,213 A | 6/1999 | Haissaguerre et al. | |
| 6,086,586 A | 7/2000 | Hooven | |
| 6,132,426 A * | 10/2000 | Kroll | 606/41 |
| 6,139,545 A | 10/2000 | Utley et al. | |
| 6,168,593 B1 | 1/2001 | Sharkey et al. | |
| 6,273,887 B1 | 8/2001 | Yamauchi et al. | |
| 6,464,704 B2 | 10/2002 | Schmaltz et al. | |
| 6,511,480 B1 | 1/2003 | Tetzlaff et al. | |
| 6,585,735 B1 | 7/2003 | Frazier et al. | |
| 6,632,193 B1 | 10/2003 | Davison | |
| 6,770,072 B1 | 8/2004 | Truckai et al. | |
| 6,802,843 B2 | 10/2004 | Truckai et al. | |
| 6,843,789 B2 | 1/2005 | Goble | |
| 6,923,806 B2 | 8/2005 | Hooven et al. | |
| 7,070,597 B2 * | 7/2006 | Truckai et al. | 606/41 |
| 7,160,296 B2 | 1/2007 | Pearson et al. | |
| 7,326,202 B2 | 2/2008 | McGaffigan | |
| 7,517,349 B2 * | 4/2009 | Truckai et al. | 606/49 |
| 7,887,535 B2 | 2/2011 | Lands et al. | |
| 8,075,555 B2 * | 12/2011 | Truckai et al. | 606/41 |
| 8,512,335 B2 * | 8/2013 | Cheng et al. | 606/41 |
| 2003/0078573 A1 * | 4/2003 | Truckai et al. | 606/41 |
| 2003/0125735 A1 * | 7/2003 | Herzon | 606/51 |
| 2010/0057083 A1 | 3/2010 | Hanna | |

OTHER PUBLICATIONS

International search report dated Mar. 1, 2011 for PCT/US2011/020136.

Office action dated Mar. 5, 2013 for U.S. Appl. No. 12/783,714.

* cited by examiner

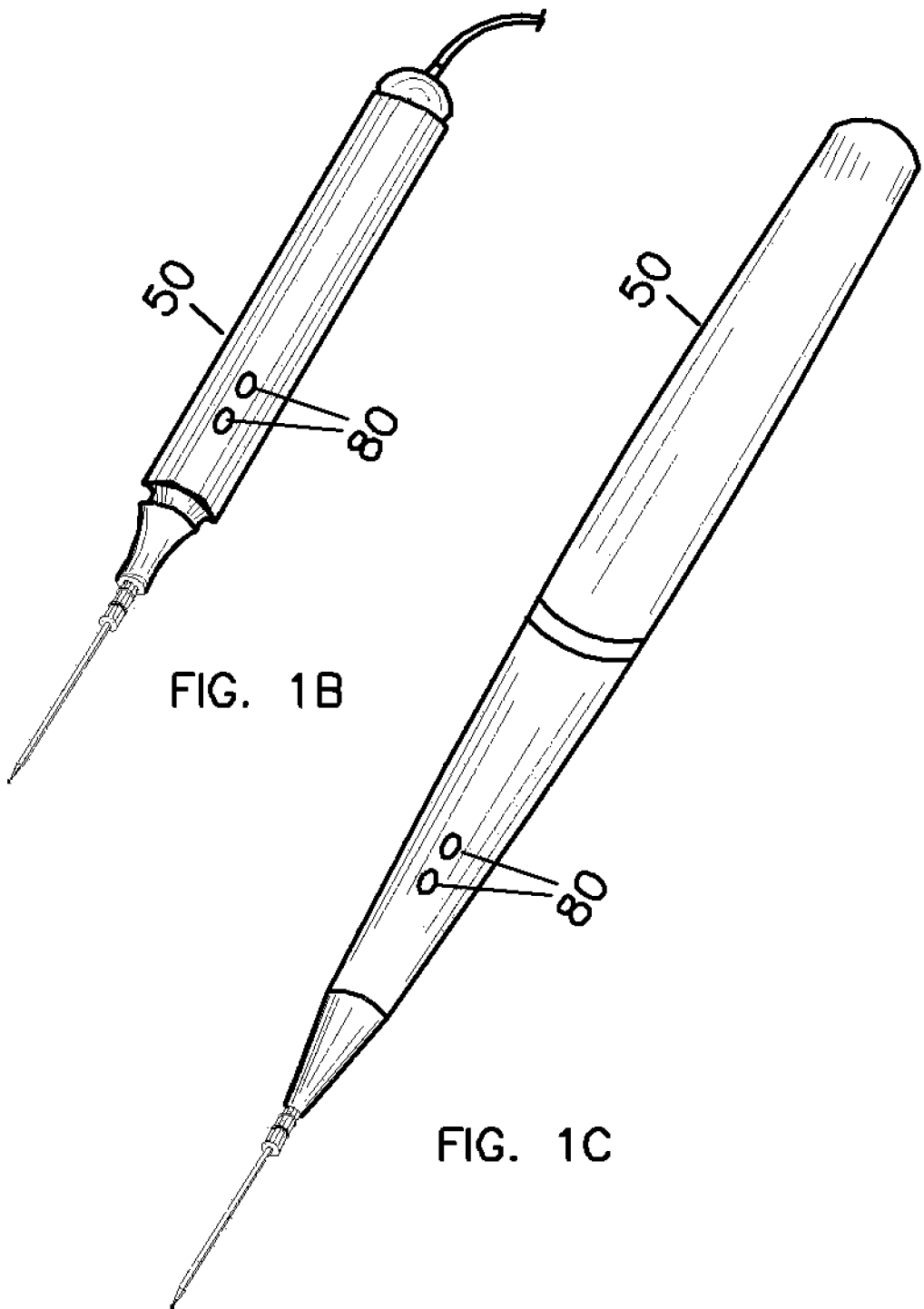

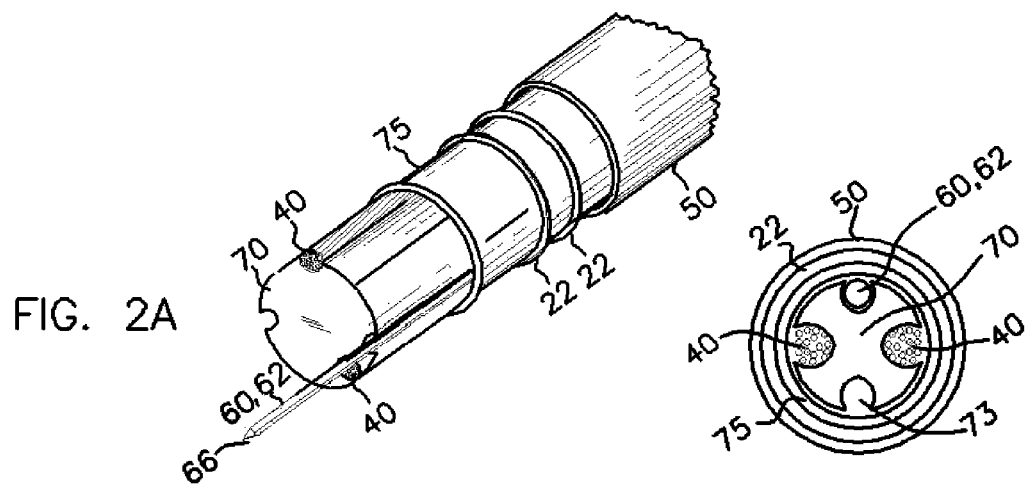
FIG. 2A
FIG. 2B
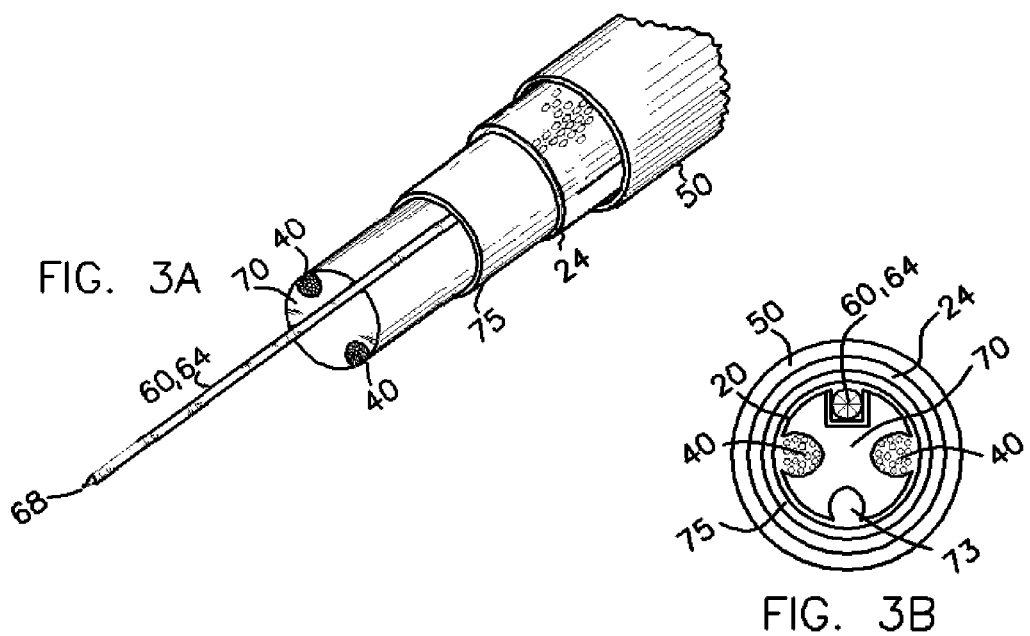
FIG. 3A
FIG. 3B

MEDICAL HEATING DEVICE AND METHOD WITH SELF-LIMITING ELECTRICAL HEATING ELEMENT

BACKGROUND OF THE INVENTION

1. Field of the Invention

This invention relates to medical heating devices comprising a probe that causes heating of target tissue for tissue ablation, tissue cutting, or tissue shrinking, and, in particular, to the heating and temperature control of such devices and their probes. The probe cauterizes tissue as it ablates, cuts, or shrinks. Cauterization is the process of destroying tissue using heat conduction from a metal probe heated by electric current where the heating stops bleeding from blood vessels in soft tissue. The invention may be used in medical, dental, and veterinary procedures involving soft tissue ablation, cutting, or shrinking.

2. Description of Related Art

Medical heating devices are presently used for selected tissue ablation in a number of treatment regimens. Typically, the heat is generated using radiofrequency-induced arcing between two points or by electric current conduction through the body to a grounding device. Examples include those describe in U.S. Pat. Nos. 6,132,426 and 6,969,644. One problem with electric-arc-based heating devices is the danger of electrical fires that can occur in a medical practice, operating suite, or hospital. Current conduction devices lack sufficient control over the path the current takes through the tissue from source to ground. The amount of tissue heating that occurs is also difficult to control, potentially leading to unnecessary injury as a side effect to the treatment.

Other prior art medical heating devices use standard electrical heating elements that are thermostatically controlled with switches or thermocouples. These devices control heat production and probe temperature essentially by switching the electrical heating element fully on or fully off, resulting in a temperature fluctuation of the ablation or cutting probe of the medical device that is more than optimal for tissue ablation or tissue cutting purposes.

A self-limiting medical heating device that offers much better control over the location and amount of tissue heating, as well having safety improvements to both the patient and operator is highly desirable.

BRIEF SUMMARY OF THE INVENTION

A medical heating device is provided with an electrical heater element formed out of a self-limiting conductive material. The self-limiting conductive material may be a conductive polymer or conductive ceramic material characterized by an electrical resistance that varies with temperature, such that heat production from electrical current through the material automatically varies with temperature. A thermally insulating jacket contains the heater element, which can be coupled, e.g., by wiring, to an electrical power supply. A thermally conductive probe extends outward from the jacket and is thermally coupled to the electrical heater element formed out of a self-limiting conductive material. The medical heating device may be used in a method wherein the end of the probe is touched to target tissue, whether for thermal ablation, cutting, or shrinking of the tissue or, if the probe is a hollow tube, for applying a heated material to the target tissue. Because the temperature of the probe is self-limiting due to the temperature-dependent resistance of the conductive material used for the heater element, overheating and/or under heating of the target tissue is avoided.

BRIEF DESCRIPTION OF THE DRAWINGS

FIGS. 1B and 1C are perspective views of alternative forms of hand piece in accord with the present invention.

FIGS. 2A and 3A are partially cut-away perspective views of a probe distal end of first and second embodiments of medical heating device respectively, illustrating two different heating element arrangements. FIGS. 2B and 3B are cross-sectional views of FIGS. 2A and 3A.

DEFINITION LIST

Figure 1A:
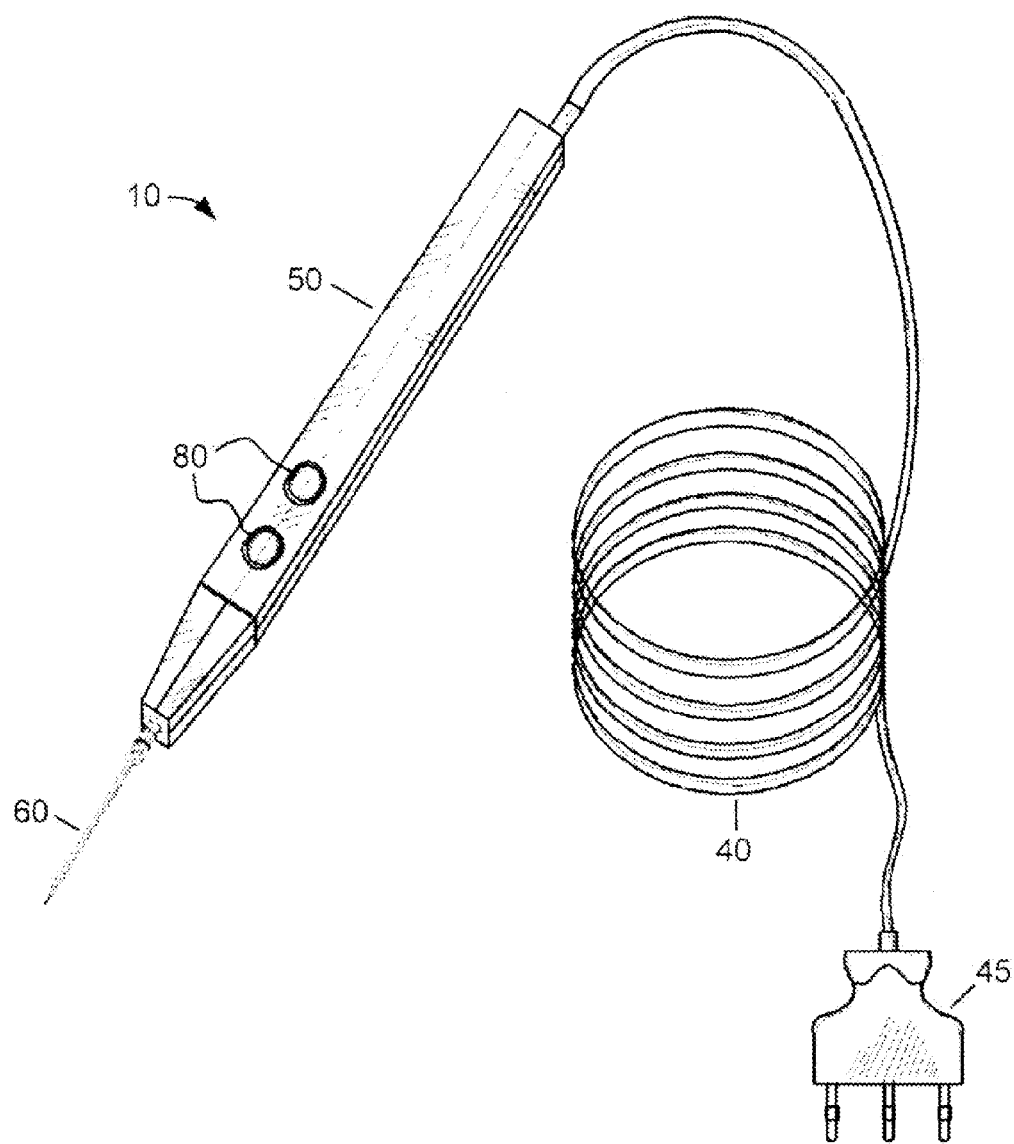
FIG. 1A is a perspective view of an exemplary hand piece which includes self-limiting electrical heating element, insulating jacket, cutting probe, and circuit connection to the power source.

| Main Term | Definition |
| --- | --- |
| 10 | Medical heating device |
| 20 | Self-limiting electrical heating element |
| 23 | Electrical heating element |
| 26 | Thermistor |
| 30 | Electrical power supply |
| 40 | Electrical wire circuit connection |
| 50 | Thermally insulating jacket |
| 60 | Thermally conductive probe |
| 70 | Core electrical spacer |
| 75 | Rim electrical spacer |
| 80 | On/off switch |
| 90 | Sensor |

DETAILED DESCRIPTION OF THE INVENTION

Medical heating device 10 comprises: a self-limiting electrical heating element 20 electrically coupled to a power source 30 by an electrical wire circuit connection 40. Medical heating device 10 further comprises: a thermally insulating jacket 50, a thermally conductive probe 60, and a core electrical spacer 70, as discussed below.

Self-limiting electrical heating element 20 behaves electrically like a standard electrical heating element in serial connection with a thermistor. Thus, on FIG. 6, self-limiting electrical heating element 20 is represented by an electrical heating element symbol 26 in serial connection with a thermistor symbol 23. The thermistor property, in effect, regulates electrical current through the electrical heating element property. In reality, self-limiting electrical heating element 20 is one electrical component, consisting essentially of a homogeneous blend of different materials, including a base material and a conductor dopant.

Self-limiting electrical heating element 20 behaves like an electrical heating element 26 because the heat it produces results primarily from electron, ion, or other charged-particle collisions occurring inside of the heating element. Heat causing collisions are induced by an electric field across the heating element resulting from an electrical wire circuit connection 40 through the heating element to an electrical power supply 30 with voltage V and current I. See FIG. 6. This phenomenon is known as ohmic heating, joule heating, or resistive heating. As with ohmic heating, the amount of heat Q produced from this invention is proportional to the square of the electrical current passing through the self-limiting electrical heating element 20, i.e. $Q \approx I^2$.

Self-limiting electrical heating element 20 behaves like a thermistor 23 because its electrical resistance R varies as a function of temperature T, which is the definition of a thermistor. Since this relationship is typically nonlinear, we use log scales of resistivity to more easily demonstrate its relationship with temperature. If resistance increases with increasing temperature, the device is called a positive temperature coefficient (PTC) thermistor or posistor. If resistance decreases with increasing temperature, the device is called a negative temperature coefficient (NTC) thermistor. Resistors are designed to have constant resistance over a wide temperature range and are sometimes called zero temperature coefficient (ZTC) materials, which could be another subset of thermistor.

Acting in tandem, these two properties regulate temperature of the self-limiting electrical heating element 20. Changes in the temperature of the medical cutting device, caused by using the device, in turn, result in resistance changes. Resistance is inversely proportional to current, i.e. $R \approx 1/I$. As stated above, heat produced is proportional to $I^2$, thus, $Q \approx 1/R^2$. Therefore, small changes in resistance yield relatively large changes in heat production from the self-limiting electrical heating element 20. There is a maximum R, however, where resistance becomes too large to allow an electrical circuit connection between the power source and the heater element aspect of 20. Above this temperature, the heater is shut off, resulting in rapid cooling.

Figure 7:
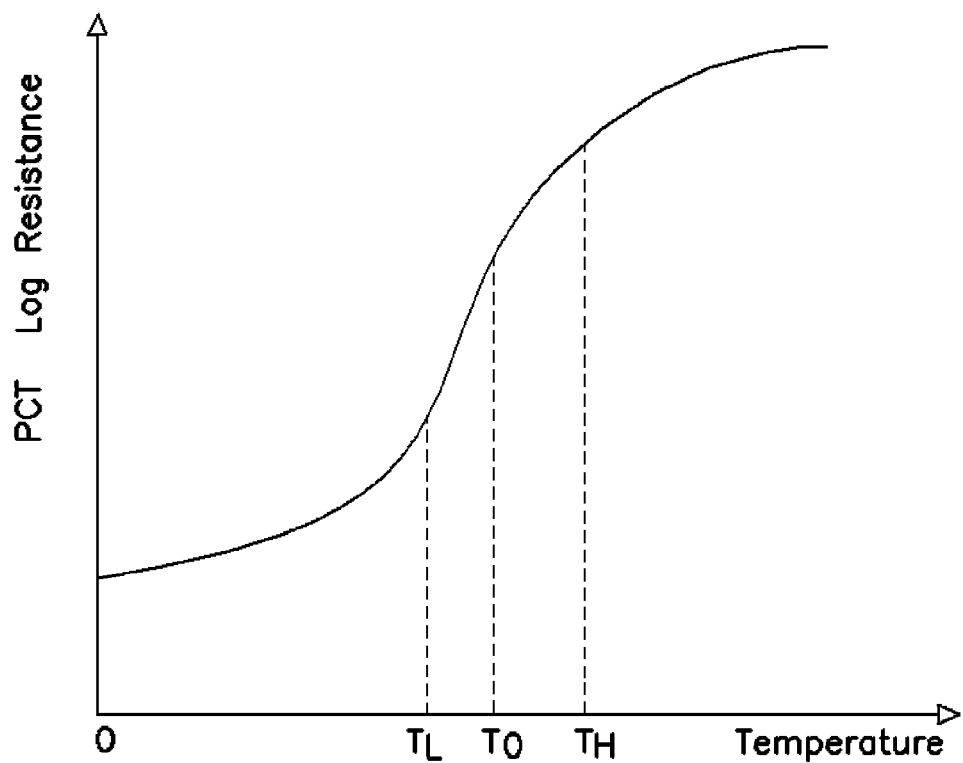
FIG. 7 is a logarithmic graph of electrical resistance (ohms) versus temperature (C) for best-mode material of self-limiting electrical heating element.

In best mode, self-limiting electrical heating element 20 is made of PTC material. FIG. 7 is a graph of the electrical resistivity versus temperature of a PTC heater material suitable for our purposes. Suitability is marked by a resistivity that gradually increases with temperature as noted by the mid-level positive slope character of the graph. Further, there is an inflection point in the graph at $T_0$. As temperature rises above $T_0$, resistivity increases at a decreasing rate with temperature. Thus, there is a gentle heat production decrease at a decreasing rate as temperature rises above $T_0$. As temperature falls below $T_0$, resistivity decreases at a decreasing rate with temperature. Thus, there is a gentle increase in heat production at a decreasing rate as temperature falls below $T_0$. With reference to FIG. 7, going from $T_0$ to $T_H$, resistivity gradually increases, thereby decreasing heat production, thereby cooling the heater element back to $T_0$. Likewise, going from $T_0$ to $T_L$, resistivity gradually decreases, thereby increasing heat production, thereby heating up the heater element back to $T_0$. There is a mathematically stable temperature point at $T_0$, otherwise known as an inflection point. Materials with this inflection point relationship yield perfect characteristics for best mode because this yields optimal stability to keep the device very steadily set at $T_0$. Thus, PTC heaters are capable of "automatic temperature control" or an inherently stable temperature $T_0$ when it is placed in an electric field strong enough to induce heat-producing current. Furthermore, the steady state temperature remains at $T_0$ across a wide range and fluctuation of voltages from direct current or alternating current power supplies 30.

Figure 8:
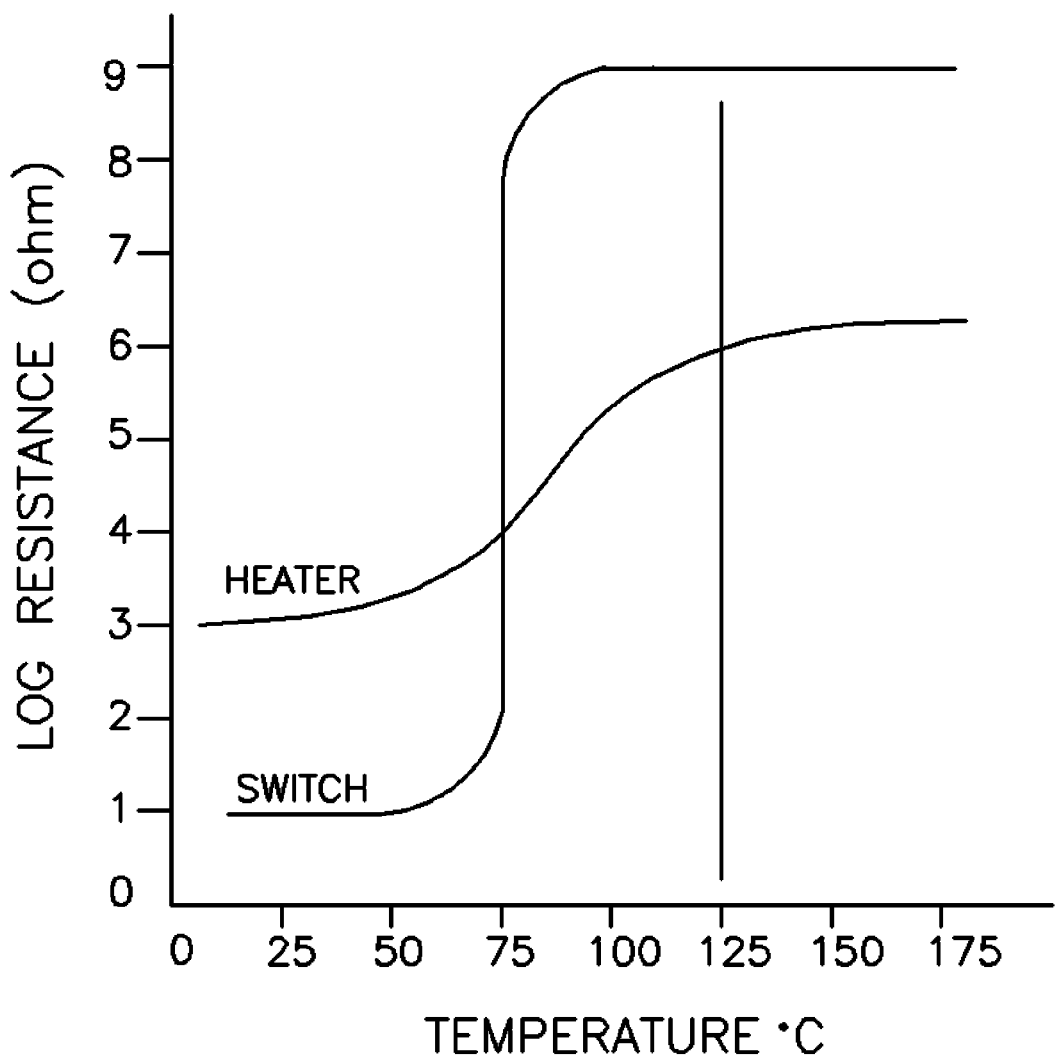
FIG. 8 is a logarithmic graph of electrical resistance (ohms) versus temperature (C) for best-mode material of self-limiting electrical heating element along with that of a thermocouple switch for comparison purposes.

An standard electrical heating element combined with a "thermostat switch" or thermocouple results is a somewhat similar type of temperature oscillation around $T_0$ however the switch method results in much more radical temperature fluctuations around $T_0$ as compared to that of self-limiting electrical heating element 20. See FIG. 8. $T_0$ is 75° Centigrade in FIG. 8. With a switch, the heater is either on fully on or off completely. As a result, the heater continuously cycles from extreme high heat production to zero heat production while zeroing in on target temperature $T_0$. On the other hand, with this invention, electrical resistance only gradually changes with temperature, thereby only gradually changing heat production while technically oscillating extremely slightly around target temperature $T_0$.

Below the transition temperature $T_0$, the composition used for the switch has a very low resistance, on the order of 10 ohms or less. Thus the switch turns the heater on full blast at temperature just below $T_0$. On the other hand, the composition used for self-limiting electrical heating element 20, only drops to about 1000 ohms, thereby causing only a slight increase in heat production at the same temperature. Above the transition temperature, the composition used for the switch has a very high resistance, on the order of $10^9$ ohms or higher. Thus the switch turns the heater completely of While the self-limiting electrical heating element composition used for the heater has only a slightly higher resistance at this temperature, thus heat output only slight decreases. Moreover, with medical heating devices, this temperature fluctuation is exacerbated as the device may incur a large heat sink while in full contact with tissue at one instant and an instant later incur no heat sink with the device at rest only in contact with air. This invention yields a medical heating device with a much more constant target temperature as compared to prior art switch operated medical heating devices, even while allowing for rapid fluctuation of heat sink activity associated with tissue ablation or cutting.

The inflection point relationship between resistivity and temperature of PTC material is further preferred because it results in a self-limiting electrical heating element 20 with a relatively small temperature deviation around $T_0$ of only a few degrees, e.g. 3-10 degrees centigrade. Thus if $T_H$ and $T_L$ were the respective maximum and minimum temperatures of the heater system when subjected to medical use, $T_H$-$T_L$ would be much less for self-limiting electrical heating element as compared to the switch operated medical heating device element. In best mode, $T_H$-$T_L$ is only 3-5 degrees centigrade or so, depending on the choice of PTC material used in the medical heating device.

Different tissue ablation or cutting procedures may require different optimal temperature operating ranges. For instance, different procedures may require different shaped and sized cutting probes, thereby changing heat sink requirements, thereby changing the heat production and temperature ranges of the medical heating device. Different target tissues are ablated in different procedures, which may require different optimal cutting temperature ranges of the medical heating device for each procedure. Thus, certain tissue ablation or cutting procedures may require different target temperatures $T_O$ with different operating ranges $T_H$ to $T_L$. These criteria may be adjusted by carefully choosing a PTC, NTC, or ZTC heater material for the self-limiting electrical heating element 20 with the best resistance temperature graph. Further, various dopants and various concentration of dopants may be used to vary characteristics to yield different resistance temperature graphs. Further combinations of PTC, NTC, and ZTC materials may be used to yield different resistance temperature graphs. Many of these materials are currently commercially available.

Figure 9A:
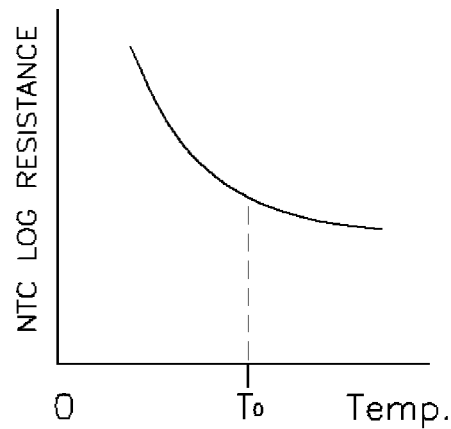
FIGS. 9A, 9B, 9C, and 9D depict logarithmic graphs of electrical resistance (ohms) versus temperature (C) of a NTC, a ZTC, a NTC/ZTC blend material, and a PTC/ZTC blend material.
Figure 9B:
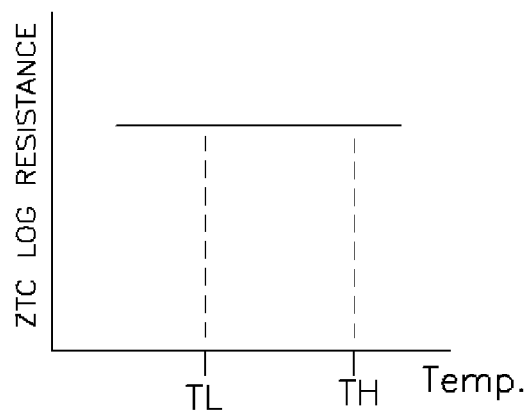
Figure 9C:
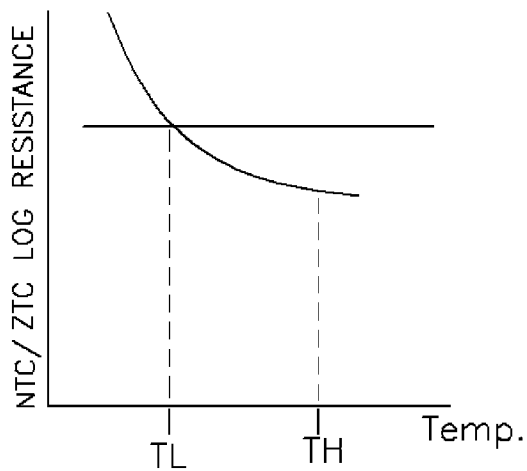
Figure 9D:
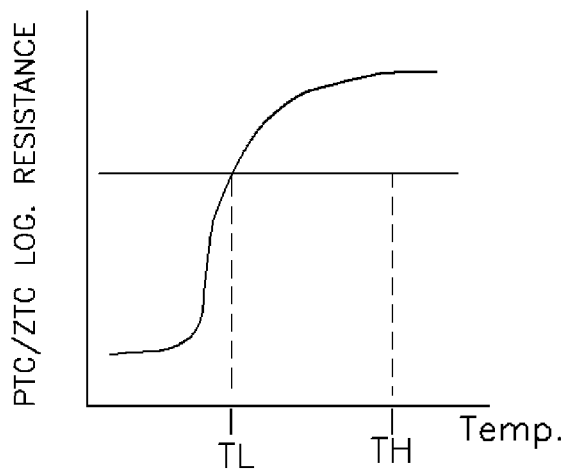

FIG. 9A includes the resistance temperature relationship of a NTC material. This arrangement may be used to create an operating temperature $T_O$ with sharp cut-off at such temperature. FIG. 9B includes the resistance temperature relationship of a ZTC material. This arrangement may be used to create a constant heat output at a certain level across a wide range of temperatures $T_H$ to $T_L$. FIG. 9C includes the resistance temperature relationship of a NTC/ZTC blend material. This arrangement may be used to create a wide operating temperature range of $T_H$ to $T_L$ with constant heat output at a certain level but with sharp cut-off at temperature $T_L$. FIG. 9D includes the resistance temperature relationship of a PTC/ZTC blend material. This arrangement may be used to create a wide operating temperature range of $T_H$ to $T_L$ with constant heat output at a certain level but with sharp increase in heat production at temperature $T_L$ thereby preventing the probe temperature from ever falling below $T_L$.

Figure 6:
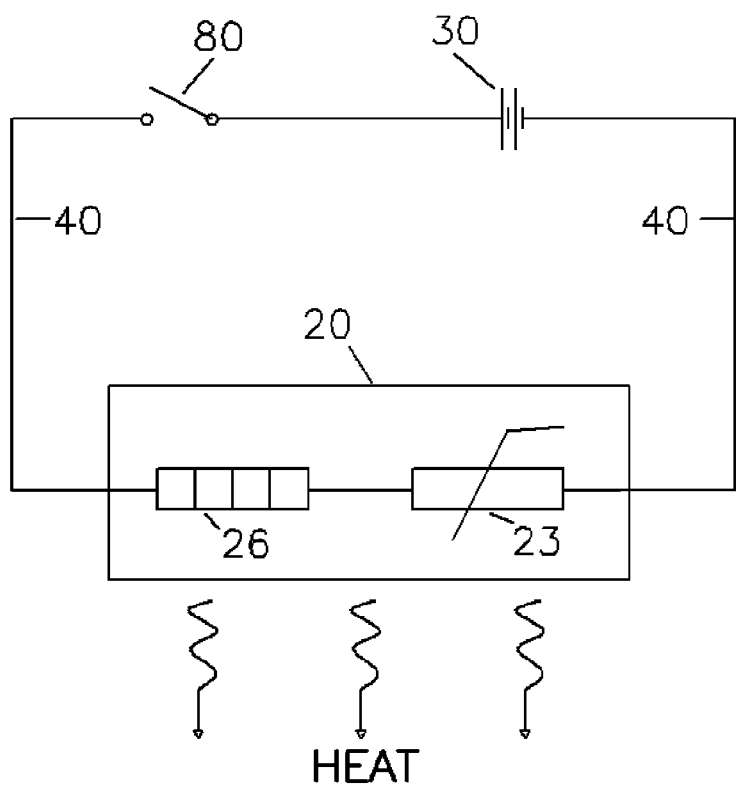
FIG. 6 is a circuit diagram of medical heating device.

PTC, NTC, and ZTC materials can be made from a crystalline or semi-crystalline polymer base material with certain conductive "doping" material added. With polymer based thermistors, transition temperature results from the melting or freezing of polymer molecules. With crystalline or semi-crystalline polymers, molecular structure is more tightly packed in solid phase and less tightly packed in liquid phase. Polymer molecules are generally non-conductive, so a conductive dopant must be added to make the material conductive. At temperatures below $T_O$, most polymer molecules are in solid phase, thus closely packed, thus at their most conductive state or level. At temperatures above $T_O$, most polymer molecules are in liquid phase, thus loosely packed, thus at their least conductive state or level. For the same choice of a matrix polymer, transition temperatures $T_O$ generally coincide with the polymer softening point of the selected matrix polymer. In FIG. 6, both switch and heater are made from the same type of polymer material, thus they have the same transition temperature $T_O$.

Figure 10:
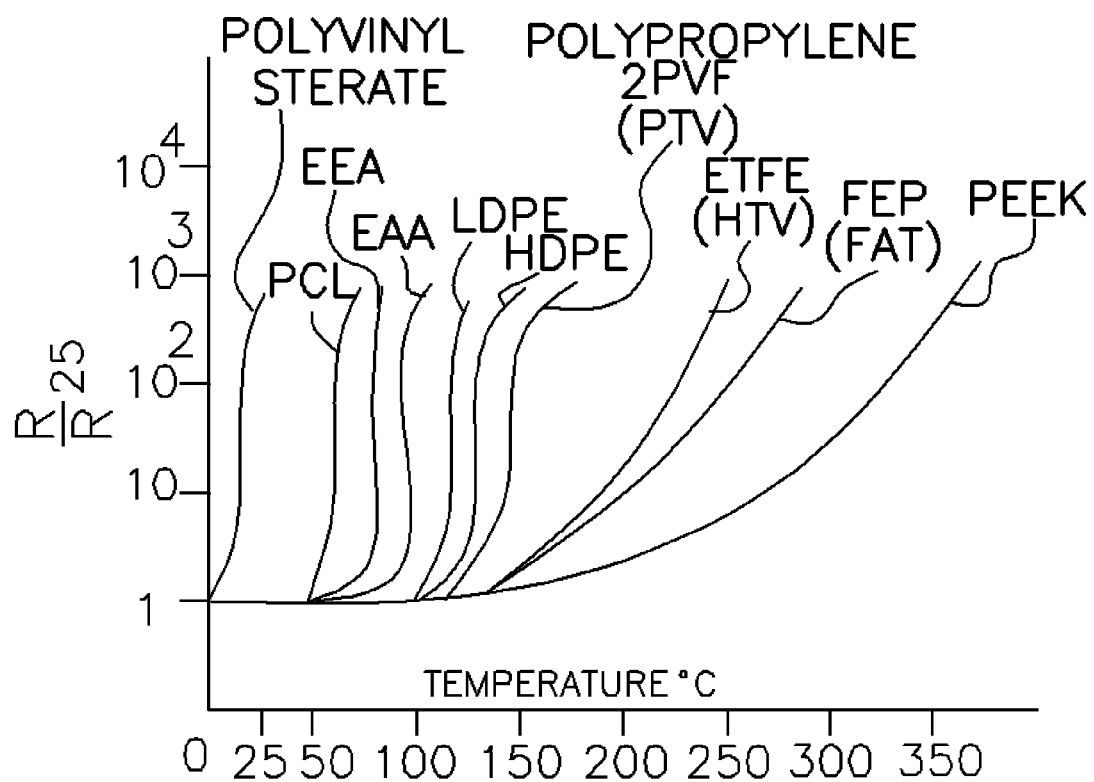
FIG. 10 is a logarithmic graph of electrical resistance (relative to resistance at 25° C.) versus temperature (C) for various conductive polymer base materials with different polymer softening points, for use in selecting an appropriate conductive polymer material for a specified tissue ablation or tissue cutting application.

Materials having these properties are known and commercially available with a range of transition temperatures $T_O$. FIG. 10 illustrates different transition temperatures for a number of possible polymer matrices for a conductive polymer composition. Thus, successively increasing transition temperatures are seen for conductive polymers made using matrices of polyvinyl sterate, polycaprolactone (PCL), ethylene ethylacrylate (EEA), low-density polyethylene (LDPE), high-density polyethylene (HDPE), polypropylene (PP), polyvinylidenefluoride (PVF2), polyvinylfloride (PVF), ethylene tetrafluoroehylene copolymer (ETFE), ethylene perfluoroalkoxy copolymers (PFA), tetrafluoroethylene/hexafluoropropylene copolymer (FEP), etc. The following table shows crystalline melting points for several polymers. Conductive polymer compositions usable with the present invention may include any of these polymers as well as those described in U.S. Pat. Nos. 4,514,620 and 5,554,679. PTC, NTC, and ZTC materials can also be made from blending two or more conductive polymers.

| Polymer Type | Melting Point (C.) |
| --- | --- |
| Vestenamer™ 8012 (cyclooctane polymer) | 40-55 |
| Ionomers | 85-99 |
| Ethylene Vinylacetate (EVA) | 103-106 |
| Low-Density Polyethylene (LDPE) | 105-110 |
| Linear Low-Density Polyethylene (LLDPE) | 122-124 |
| Polybut-1-ene 126-127 | 126-127 |
| High-Molecular-Weight Polyethylene (HWPE) | 125-132 |
| Ultra-High-Molecular-Weight Low-Density Polyethylene (UHMWPE) | 125-135 |
| High-Density Polyethylene (HDPE) | 130-135 |
| Elastomer Blend | 160-165 |
| Polypropylene (PP) | 160-165 |
| Block Copolymer of PP | 160-165 |
| Polyvinylidene Fluoride (PVF2) | 160-165 |
| Polyamide 12 (PA12) | 180 |
| Polyamide 11 (PAII) | 185 |
| Copolymer of Polyamide | 160-220 |
| Thermoplastic Fluoroelastomer | 160-220 |
| Thermoplastic Elastomer | 185-202 |
| Ethylene-Chlorotrifluorethylene Copolymer (ECTFE) | 190-191 |
| Polyamide 610 (PA610) | 215 |
| Polychlorotrifluoroethylene (PCTFE) | 215-216 |
| Polyamide 6 (PA6) | 220 |
| Polybutyleneterephthalate (PBT) | 220-223 |
| Polycarbonate (polyester) | 200-260 |
| Poly-4-methylpent-1-ene | 230-240 |
| PA 6-3-T | 240 |
| Polyamide 66 (PA66) | 255 |
| Polyethyleneterephthalate (PET) | 250-265 |
| Ethylene-Tetrafluoroethylene copolymer (ETFE) | 270-271 |
| Perfluoroalkoxy copolymer (PFA) | 250-305 |
| Fluoroethylene-propylene copolymer (FEP) | 290-291 |
| Polytetrafluoroethylene (PTFE) | 325-327 |

Dopant material is added to base material in order to render it conductive which allows the material to perform like a heating element. Also dopant is added to slow the resistance change or to widen the graph discussed above. Dopants are conductive material such as carbon black, metal oxide, semiconductor material, blends thereof, or other material that is conductive and capable of being produced in small particles. The specific resistivity temperature relationships of PTC, NTC, and ZTC materials are arrived at by varying the type and concentration of dopant. For instance, the switch in FIG. 8 has the same type of dopant as the self-limiting electrical heating element but the self-limiting heating element has a much smaller and evenly dispersed concentration of the dopant. Thus, a lower concentration or density of conductive particles in the polymer base composition is one way to obtain the desired gradual change in resistance for a self-limiting heater element. Generally speaking, dopant levels above 50 percent yield switch type material, dopant levels of 15-40% yield thermistor material, and dopant levels of 10% yield electro magnetic interference and or electrostatic discharge. Also, porosity, surface area, particle size, and oxygen content, of the conductive dopant may be varied to produce various properties. Also, more than one type of dopant may be added to base material. Either the base material molecules or the dopant material particles may actually cause the ohmic heating. Thus, dopant may function to produce electron transfer or vibrational heating or both. All of these factors together with various carbon black loading levels and others results in a near endless amount of combinations between type(s) and amount(s) of dopant along with type(s) of base material to yield a near endless amount of specific resistivity temperature relationships.

PTC, NTC, and ZTC materials can also be made from a ceramic material or ceramic based material with conductive dopant added. Ceramic material can be conductive or not conductive depending on phase. Ceramic material can be engineered to change phase from solid to liquid or liquid to solid at specific temperatures $T_0$. Typically, ceramic base material is barium titanate and/or related divalent titanates and zirconates. Typical dopants include lead, strontium, rare earth metals, antimony, bismuth, or similar. Dopants are added to increase or decrease the anomaly range of the base material or further adjust the slope of the resistivity temperature relationship. Various ceramic thermistor heaters with different temperature resistivity relationships are commercially available. Also, a ceramic thermistor heater material manufacturer may endeavor to undertake special development programs to deliver specially desired characteristics.

Typically, self-limiting electrical heating element 20 specification or design starts with the requirement of the medical procedure to determine the desired operating temperature range for the particular tissue ablation to be performed. Then, a search is conducted to find the proper self-limiting electrical heating element material, whether PTC, NTC, ZTC or combination thereof, to yield this temperature range. Note that size, shape, and conductivity of both probe and insulating material and other factors influence the operating temperature range of the probe and heater. All influential aspects are factored into a calculation performed to yield the desired resistance temperature graph. Then the best commercially available thermistor material is chosen with the best resistance temperature graph to fit the specific medical procedure desired.

Physical form of self-limiting electrical heating element 20 may consist of one or more coils 22 that are wound around a core electrical spacer 70. See FIG. 2A. The core electrical spacer 70 keeps electrical wire circuit connection wires 40 spaced apart to prevent an electrical short. Individual loops 22 of heating element 20 can be connected in parallel to electrical wire circuit connection wires 40 so as to provide a set of electrical current paths through loops 22. Alternatively, the two end loops 22 of heating element 20 could be connected to wires 40 to yield a current path along the entire length of heater 20.

As seen in FIG. 2B, core electrical spacer 70 has a cross-section that accommodates lengthwise passage of the wires 40 as well as one or more thermally conductive probes 60 or possibly also a sensor (not shown here). In particular, core electrical spacer 70 may have a set of lengthwise indentations 73 having shapes that closely match the respective wire 40, probe 50 or sensor components 90 that are received therein.

Self-limiting electrical heating element 20 may alternately consist of a sheet form 24 of material wrapped as a blanket around core electrical spacer 70. Sheet 24 is connected along the length wire electrodes 40 in a manner that provides parallel electrical current paths through the entire sheet 24. Another possible arrangement would be to simply have one wire 40 contact the sheet 24 at the distal end and the other wire 40 contact the sheet at the proximal end.

Yet another alternative would be to employ a core electrical spacer 70 that is itself made from the self-limiting conductive material. As wires 40 extend through the entire length of core spacer 70, current would flow in parallel through the bulk of the spacer material to produce heat. A number of commercially available self-regulating heater cables, marketed for use as storage tank heaters, ground heaters, in pipe freeze protection or for domestic hot water temperature maintenance, have such a construction, such as those manufactured by Tyco Thermal Controls, LLC under their Raychem brand.

In such a construction, probe 60 would need to be electrically insulated from the conductive spacer material 70, e.g., by having an electrically insulating cladding.

In addition to core electrical spacer 70 there may be another electrical spacer called a rim electrical spacer 75. Rim spacer 75 is an electrical insulator in some areas and thermally conductive in other areas. Electrical insulating material would be required between all portions of self-limiting heater 20 and circuit connection wires 40 where conductivity is not desired. This pattern would be different for a serial heater connection as compared to a parallel heater connection. For instance, in FIG. 3A, there would be a longitudinal slit down the full length of rim spacer 75 to provide parallel loop connection discussed above. Also, rim electrical spacer 75 would be required to be thermally conductive in other areas, e.g. near the probe so that heat may freely transfer from heater 20 to probe 60 between rim spacer 75.

Thermally insulating jacket 50 can be the exterior surface of the hand-piece or handle. Jacket 50 functions to insulate the heat produced by heating element 20 to keep heat inside the device and provide a non-heated handle for the user to easily control the tissue ablation device. Although not depicted in drawings, jacket 50 extends all the way down to cover core electrical spacer 70. Best mode medical heating device 10 is depicted in FIG. 1A. In this mode, thermally insulating jacket 50 has exterior shape similar to a pen. This shape is believed to deliver superior control and feel of the device as a scalpel-type device. Another mode is depicted in FIG. 1B where the pen-like jacket form of FIG. 1A is replaced by a jacket having a thicker handle much like handles found on a screwdriver. Jacket 50 may take whatever exterior form that proves most desirable for the user. Exterior form does not affect self-limiting nature of the invention.

In best mode, thermally insulating jacket 50 further comprises an electric field cover layer. Cover layer is a layer of jacket 50 that completely covers all electronic circuitry in the hand piece. Cover layer can be made of metal or high resistance material with resistivity on the order of $\log 10^{10}$ ohm-cm or higher in order to contain electrical fields created by the circuitry. Thus, medical device 10 does not produce any electromagnetic interference or electro-static discharge.

Thermally conductive probe 60 extends outward from thermally insulating jacket 50 and is thermally coupled to self-limiting electrical heating element 20. Probe 60 may have any of several shapes, including a circular cross-section 62, a square cross-section 64, an oval, rectangular or other oblong cross-section, a rounded tip 66, or perhaps one with a rollerball tip, a blunt tip, a pointed or other piercing tip as 68, and may even form a hollow tube adapted to supply a fluid that has heated by the device for application onto or injection into target tissue. The probe could also have more than one needle or be multi-pronged as in fork-like probe. Likewise, the probe may be accompanied by or may include cutting, suturing or stapling capabilities, and thus may form any of several known manipulable medical tools, such as those used in arthroscopic surgery, provided it is thermally conductive to receive and transmit heat from the device's heater element. For example, the probe tip may include a tool for delivering preheated biodegradable staples or other material to target tissue. The preheated material delivered by such a tool could be used to cauterize blood vessels or ablate nerves or other tissue.

Figure 4:
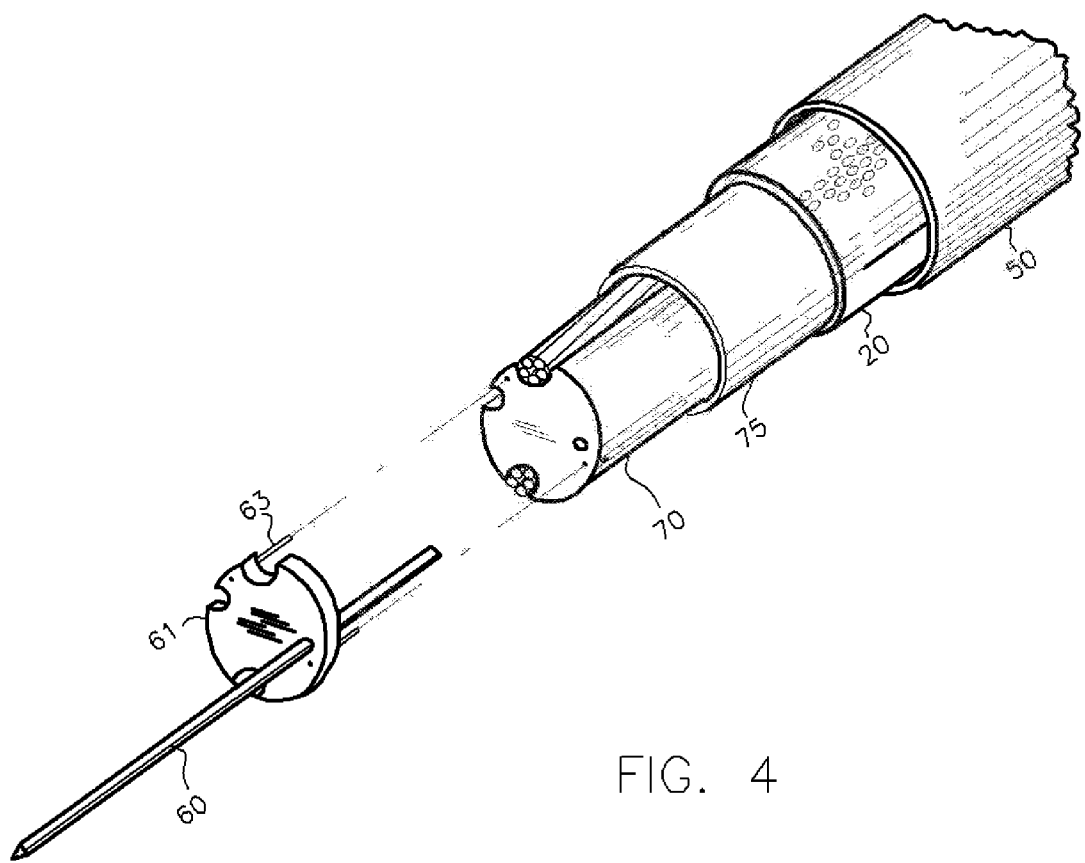
FIGS. 4 and 5 are partially cut-away perspective views of a probe distal end of third and fourth embodiments of medical heating devices respectively, illustrating the addition of a replaceable probe module in FIG. 4 and an optional sensor in FIG. 5.
Figure 5:
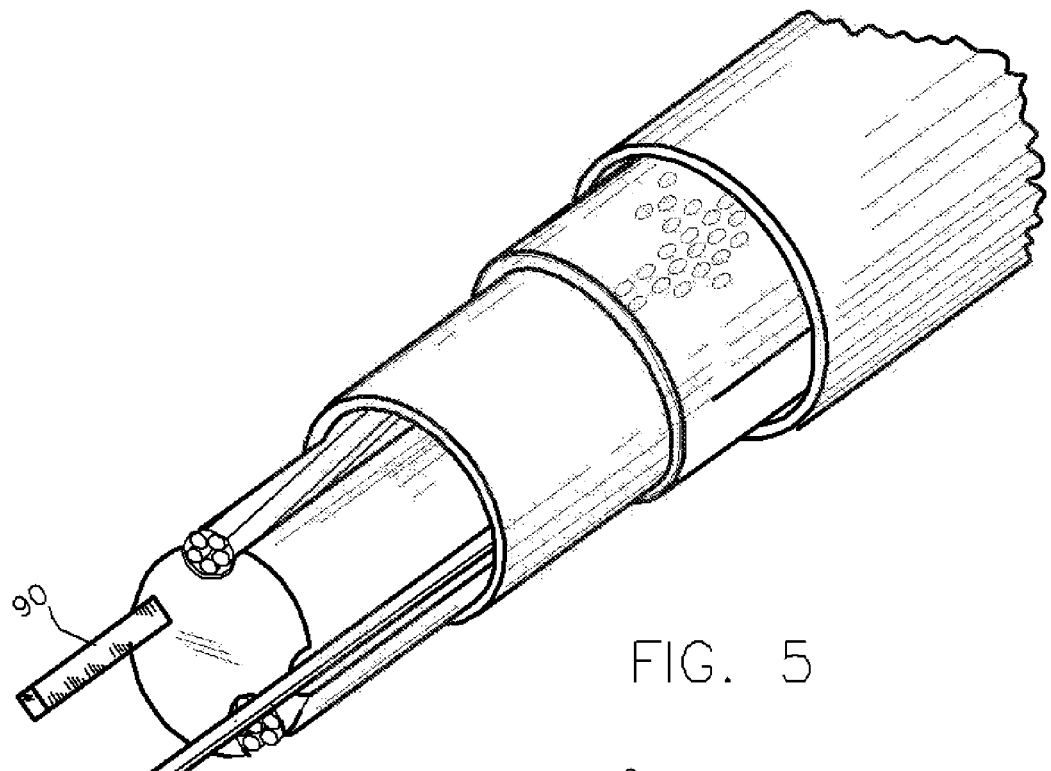
Figure 5A:
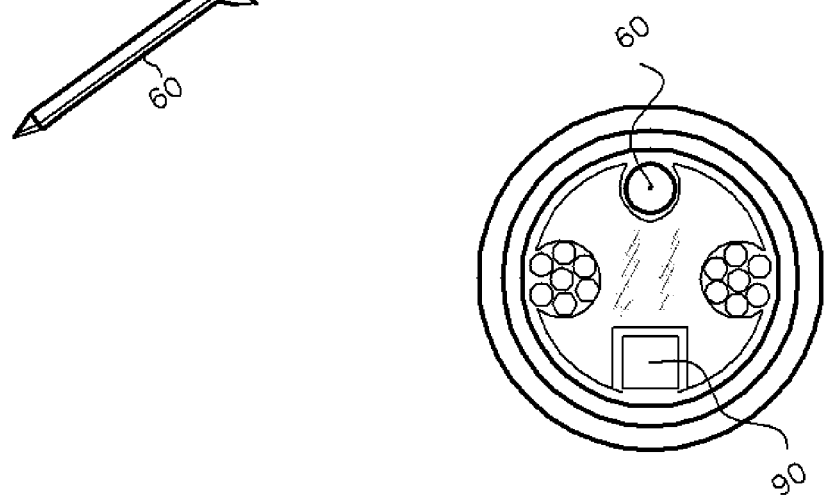
FIG. 5A is a cross-sectional view of FIG. 5.

Probe 60 may be an interchangeable module with a probe support 61 that is attached to self-limiting electrical heating element 20, thermally insulating jacket 50, or electrical spacer 70 with pins 63, screws, ratchets, spring detents, magnets, connectors, or other attachment means. FIG. 4 depicts pins 63 attachable to core 70. In any event, probe support 61 reversibly connects to the medical heating device where a variety of probes types are also fitted with the same support 61. Support 61 provides ability to quickly snap on and off different probes in order to more effectively perform a medical procedure. Interchangeability of probes offers much greater flexibility in a particular heating device's usefulness. Provided the heating requirements are similar, different medical applications can be performed using the same tool simply by swapping one probe module for another.

Probe 60 may be accompanied by at least one sensor 90, which can be an imaging device, such as a fiber-optic imager, positioned relative to the probe 60 and that can be coupled through the plug assembly to a suitable display so as to aid a user in directing the probe to a target location. Any such imaging sensor or scope may be equipped with an antifogging device or agent. Heat from self-limiting electrical heating element 20 may be used with such antifogging device or agent. Sensor 90 could also be a nerve detector. Such nerve detectors are known and used in other probe-like medical tools. Like the imager, they too can be suitably located near the probe 60, or may even be integrated into the heated probe itself for finer control over positioning.

Electrical wire circuit connection 40 creates a circuit connection between self-limiting electrical heating element 20 and electrical power supply 30. Electrical power supply 30 may be standard 110VAC, AC battery, DC battery, solar cell, or custom power source module that is itself power by any of the preceding. None of these is depicted in drawings because the specific power supply is not an essential element of the invention. With FIG. 1A, power source 30 is not shown. Electrical circuit connection 40 may have a connector 45 which is reversibly attachable to power source 30. Thus, power source 30 has a connector that is reversibly connectable to connector 45. With FIG. 1C, power source 30 and electrical wire circuit connection 40 are completely contained inside of thermally insulating jacket 50. Thus, medical heating device 10 has a wireless mode as depicted in FIG. 1C.

Medical heating device 10 may further comprise on/off switch 80 which may be located on thermally insulating jacket 50, close to the user's hand when the device is in operation. On/off switch switches on and off electrical circuit connection 40 from power supply 30, thereby shutting off power to self-limiting heater 20.

Medical heating device 10 may be used in conjunction with other medical devices such as ultrasonic, mono-polar electro surgery, bi-polar electro surgery, suction, inflation, insufflation, microelectronic chip, fiber optic, radio frequency, microwave, infrared, X-ray, light emitting diode, resistance or wire heating, or other standard medical device capable of being installed on or near probe 60. Electrosurgery is the application of a high-frequency electric current to biological tissue as a means to cut, coagulate, desiccate, or fulgurate tissue. In electrosurgical procedures, the tissue is heated by an electric current through itself. Its benefits include the ability to make precise cuts with limited blood loss. Electrosurgical devices are frequently used during surgical operations helping to prevent blood loss in hospital operating rooms or in outpatient procedures.

A medical heating device constructed according to the present invention may be used by touching the distal end of probe 60 to target tissue, whether on the skin surface of a patient, subcutaneously or deeper. If the target tissue is skin, the maintenance temperature of the device could be chosen to be not more than 45° C. (113° F.). At such a moderate temperature the heat transfer from the probe to the skin can produce skin tightening, skin resurfacing and collagen remodeling, for dermal regeneration and cosmetic applications. This can also be accompanied by mechanical ablation of skin surface cells. Alternatively, a higher temperature could be used to cut skin, while simultaneously cauterizing any bleeding.

If the target tissue is subcutaneous adipose (fat) tissue, heat transfer through a piercing probe inserted into the skin can be used to cause selective damage to fat cells proximate to the probe end. If the target tissue is nerve tissue, heat transfer from the probe can be used to ablate a selected nerve, such as a rami of the temporal branch of the facial nerve or angular nerve that supplies innervations to the corrugator and procerus muscles of the face. This can aid in removing frown lines.

The target tissue might be glandular, as in sweat glands of the skin to treat hyperhidrosis or the tonsils in the oral cavity in performing a total or partial tonsillectomy.

The target tissue could be vascular (veins, arteries, capillaries, blood), wherein heat transfer through the probe can be used to produce local blood coagulation and cauterization of the vascular tissue. Or, at more gentle temperatures (near 37° C. body temperature), a hollow probe can inject a pre-heated fluid into the target artery or vein, e.g., for localized drug delivery.

The target tissue could be some abnormal growth, polyp or tumor, such as in the sinus or oral cavity. Here, heat transfer through the probe can ablate that tissue. Examples include: mucosal lesions found in Barrett's esophagitis, or tissue growth from nasal turbinate hypertrophy, or removal of colon or rectal polyps.

A heated medical device could also be used as part of a pain management or treatment protocol by applying heat to selected nerve or muscle tissue, e.g., to ablate sensory nerves or to stimulate blood flow in sore muscles.

Basically, a medical device constructed with a self-limiting electrical heater element in accord with the present invention can replace the present electrical-arc-based devices used for similar purposes. Any medical application requiring controlled heat delivery to selected target tissue can employ the present invention with much greater control and safety. The invention may be used in medical, dental, and veterinary procedures.

What is claimed is:

1. A medical heating device, comprising:
   an electrical power supply;
   a self-limiting electrical heating element formed out of a thermistor heater material consisting primarily of: a polymer base material with 5-40% conductive dopant material, a ceramic base material with 5-40% conductive dopant material, or a ceramic material without dopant material, wherein, said thermistor heater material is characterized by an electrical resistance that varies with temperature, wherein said variance in turn causes a variation of the heat production from said self-limiting electrical heating element;
   wherein said self-limiting electrical heating element is coupled to the electrical power supply by at least two wire connections, one connecting a positive terminal of said electrical power supply to said self-limiting electrical heating element and another connecting a negative terminal of said electrical power supply to said self-limiting electrical heating element;
   a thermally-insulating jacket containing said self-limiting electrical heating element, said jacket having an exterior shape that can be comfortably held by the user; and
   a thermally-conductive elongate probe extending outward from the distal end of said jacket and thermally coupled to said self-limiting electrical heating element so that heat generated in said heating element is transferred along a length of the probe to a distal end of the probe;

wherein the heat production from said self-limiting electrical heating element varies in such a way to cause the distal end of said thermally-conductive probe to remain in a temperature range conducive to a specific type of living tissue ablation, cutting, or shrinking medical procedure, wherein said electrical power supply comprises a direct current battery, and wherein said self-limiting electrical heating element, said electrical power supply, and said direct current battery are all contained within said thermally-insulating jacket, thus forming a wireless handheld complete version of said medical heating device.

2. A medical heating device as recited in claim 1, wherein said electrical heater element is made primarily of: positive temperature coefficient thermistor heater material; negative temperature coefficient thermistor heater material; zero temperature coefficient thermistor heater material; a combination of zero temperature coefficient thermistor heater material and negative temperature coefficient thermistor heater material; or a combination of zero temperature coefficient thermistor heater material and positive temperature coefficient thermistor heater material.

3. A medical heating device as recited in claim 1, wherein said self-limiting electrical heating element has physical form of at least one coil of said thermistor heater material wound around a core electrical spacer wherein said core electrical spacer functions to electrically separate some areas while electrically connecting other areas of said self-limiting heating element to said electrical power supply to yield an electrical current path through the length of said at least one coil.

4. A medical heating device as recited in claim 1, wherein said self-limiting electrical heating element has physical form of a sheet of said thermistor heater material wrapped around a core electrical spacer, with opposite ends of said sheet being connected to said battery to provide an electrical current path through the entire sheet.

5. A medical heating device as recited in claim 1, wherein said self-limiting electrical heating element comprises an elongated core formed from said thermistor heater material and having longitudinal channels running therethrough, electrical conductors in said longitudinal channels for electrically coupling said self-limiting electrical heating element to the electrical supply and said thermally-conductive probe, so as to provide a current path through said elongated core where the probe has an electrically-insulating sheathing covering areas of it adjacent to said self-limiting electrical heating element.

6. A medical heating device as recited in claim 1, wherein said thermally-conductive probe comprises one or more needle-shaped probes.

7. A medical heating device as recited in claim 6, wherein said thermally-conductive probe comprises at least one hollow tube adapted for delivering or removing material from the target tissue.

8. A medical heating device as recited in claim 6, wherein said thermally-conductive probe has cross-sectional shape that is circular, oval, square, rectangular, or oblong.

9. A medical heating device as recited in claim 6, wherein said thermally-conductive probe has a distal end that is: rounded, roller-balled, piercing, pointed, or blunt.

10. A medical heating device as recited in claim 1, wherein said thermally-conductive probe is in the physical form of the distal end of a standard surgical stapler so that said probe may deliver preheated biodegradable staples, clips, clamps, or anchors to the target tissue.

11. A medical heating device as recited in claim 1, wherein said thermally-conductive probe takes the form of a standard clamp, forceps, scalpel, articulating arm, flexible arm, net, web, mesh, balloon, or catheter, thereby providing a medical device with surface temperature capable or remaining steadily in said temperature range conducive to a specific type of living tissue ablation, cutting, or shrinking medical procedure.

12. A medical heating device as recited in claim 1, wherein said thermally-conductive probe further comprises a support arm that is connectable to a trocar, sheath, endoscope, or laparoscope.

13. A medical heating device as recited in claim 12, wherein said support arm further comprises a port connection to allow connection with standard endoscopic or laparoscopic instruments.

14. A medical heating device as recited in claim 1, wherein said thermally-insulating jacket further comprises: an interchangeable module on its proximal end and a means for reversibly attaching said interchangeable module to the distal end of said thermally-insulting jacket, wherein said means for reversibly attaching provides the capability to quickly remove and attach said interchangeable module.

15. A medical heating device as recited in claim 1, further comprising a sensor positioned relative to said thermally-conductive probe so as to aid the user in directing said thermally-conductive probe to a target location.

16. A medical heating device as recited in claim 15, wherein said sensor is: a nerve detector, a temperature sensor, or an electrical sensor.

17. A medical heating device as recited in claim 1, further comprising an ultrasonic, mono-polar electrosurgery, bi-polar electrosurgery, suction, inflation, insufflation, microelectronic chip, fiber optic, laser, radio frequency, microwave, infrared, X-ray, light emitting diode, resistance or wire heating medical device.

18. A medical heating device as recited in claim 1, wherein said thermally-insulating jacket is made of a material that contains electric fields produced therein thereby preventing electromagnetic interference or electrical static discharge.

19. A medical heating device as recited in claim 1, further comprising a thermocouple temperature control device to detect temperature of said self-limiting electrical heating element or said thermally-conductive elongate probe and to disconnect the self-limiting electrical heating element from the electrical power supply whenever a specified temperature is reached.

* * * * *